United States Patent [19]

Siren

[11] Patent Number: 4,793,945

[45] Date of Patent: * Dec. 27, 1988

[54] USE OF INOSITOL TRIPHOSPHATE AS A STABILIZER AND COMPOSITIONS FORMED THEREFROM

[76] Inventor: Matti Siren, Via Poporino 9, CH-6926 Montagnola/Lugano, Switzerland

[*] Notice: The portion of the term of this patent subsequent to Apr. 5, 2005 has been disclaimed.

[21] Appl. No.: 15,698

[22] Filed: Feb. 17, 1987

Related U.S. Application Data

[63] Continuation-in-part of Ser. No. 788,830, Oct. 18, 1985, Pat. No. 4,735,902.

[30] Foreign Application Priority Data

Oct. 23, 1984 [SE] Sweden .............................. 8405295
Jun. 26, 1985 [SE] Sweden .............................. 8503164
Jun. 26, 1985 [SE] Sweden .............................. 8503165

[51] Int. Cl.[4] .................... C09K 15/32; C12N 9/96; A23L 00/00; A61K 31/66
[52] U.S. Cl. .................. 252/400.2; 435/188; 426/654; 514/103
[58] Field of Search .............................. 435/188, 183; 252/400.2; 514/970, 3, 23, 44, 573, 103; 426/654, 52; 424/85, 88

[56] References Cited

U.S. PATENT DOCUMENTS 2,723,938 11/1955 Buckwalter et al. ............... 514/103
3,591,665 7/1971 Kimura et al. ............... 252/400.2 X

OTHER PUBLICATIONS

Inositol Phosphates, Their Chemistry, Biochemistry and Physiology, 1980, Elsevier Sci. Pub. Co., N.Y. (D. J. Cosgrove) pp. 3–7.
Biochimica et Biophysica, Acta (1968) 165, 1–5.
Biochem. and Biophys. Res. Comm., vol. 120, No. 2, 481–485 (Apr. 30, 1984).
Nature, vol. 306, 67–69 (Nov. 1983).
Tomlinson et al., Biochemistry, vol. 1, No. 1, pp. 166–171 (Jan. 1962).
Kerr et al., Archives of Biochemistry and Biophysics, vol. 96, pp. 347–353 (1962).

Primary Examiner—Thomas G. Wiseman
Assistant Examiner—Charles L. Patterson, Jr.
Attorney, Agent, or Firm—Scully, Scott, Murphy & Presser

[57] ABSTRACT

An organic substrate, such as a pharmaceutical or biological system subject to degradation by oxidation and/or free radical formation, is stabilized by various inositol triphosphate compounds.

21 Claims, No Drawings

USE OF INOSITOL TRIPHOSPHATE AS A STABILIZER AND COMPOSITIONS FORMED THEREFROM

REFERENCE TO RELATED APPLICATION

This is a continuation-in-part of U.S. patent application, Ser. No. 788,830 filed Oct. 18, 1985, now U.S. Pat. No. 4,735,902.

The present invention relates to a stabilized composition comprising an organic substrate, such as a pharmaceutical or biological system subject to degradation by oxidation and/or free radicals, and a method for production thereof.

It is well-known that biological materials and pharmaceuticals often have a rather limited stability even if they are stored in a dark and cold space. Among the pharmaceuticals having such a low stability, insulin, vaccine, hyaluronic acid, intralipid and prostaglandin can be mentioned. In addition, many other organic substrates susceptible to oxidative or free radical degradation are well-known to those skilled in the art and include e.g., fats, oils, ethylenically unsaturated compounds, derivatives and polymers e.g. acrylate compounds and resins, polyvinylacetate, polyvinylpyrrolidone, vinylacetate, vinylpyrrolidone and the like.

It is well-known that the formation of free radicals during storing and/or use of many pharmaceuticals and biological materials causes a degradation of these products. The free radicals namely cause an oxidation, which in its turn results in a degradation of the pharmaceutical or the biological material. Similar mechanisms are responsible for the lack of stability of other organic substrates, such as those mentioned above.

Accordingly, the presence of free radicals can explain why hyaluronic acid for example is effective at application of eyes but not at injection in joints for treatment of rheumatism. Free radicals are formed in the eyes to a slight extent. However, on the other hand, in the joints, free radicals are formed in a considerable amount. Therefore, the hyaluronic acid is broken down or degraded by free radicals in the joint fluids before it has given the desired effect.

In addition to the negative effect on the stability of pharmaceuticals and biological materials, free radicals can also increase the toxicity of said products, which of course is a very serious problem.

A very intensive research effort has been carried out for many years to find an effective and non-toxic stabilizer for organic substrates, such as pharmaceuticals and biological materials. In general, said work has not given the desired result.

In the U.S. Pat. No. 2,723,938 another kind of stabilization than that according to the present invention is disclosed. Thus, according to said patent the use of inositolhexaphosphates (IP$_6$), especially sodium phytate for stabilizing dispersability of aqueous suspensions of insoluble penicillin even after prolonged storage is shown. The use of said sodium phytate is said to insure that brief manual shaking will restore a state of complete and uniform dispersion of the penicillin. However, no effectiveness in stabilization against oxidative degradation caused by free radicals is reported. When compared with IP$_3$ stabilizers of this invention, IP$_6$ is found to be less effective as a stabilizer against degradation of organic substrates. In addition, the use of IP$_6$ is also seriously limited because of the impact on the mineral balance in animals including humans, thus limiting use thereof in compositions to be administrated to human hosts.

According to present invention a stabilized composition comprising organic substrates such as pharmaceuticals and biological systems has been provided. The stabilized composition is characterized in that it contains inositoltriphosphate, IP$_3$, in a stabilizing amount.

The appropriate stabilizing amount of IP$_3$ should be determined by routine experimentation to obtain optimum values. For example accelerated aging test can be performed with a test substrate at various levels of IP$_3$ and the optimum level be determined thereby. In general, at least 0.001% by weight of IP$_3$ based on the weight of the composition will provide some beneficial effect. Usually from 0.01-2% by weight will be employed.

The stabilizer is mainly intended to be used against degradation caused by free radicals. Such free radicals can be formed in different ways, for instance by metals, such as iron, aluminium and cadmium, and by radiation.

However, the stabilizer is intended also to be used against degradation caused by oxidation and hydrolysis. The oxidation can be caused by free radicals as mentioned above. However, oxidation can depend on other mechanisms too. Therefore, the invention covers stabilization against oxidation, hydrolysis or radiation, whatever mechanism lies behind said reaction.

The stabilizer can be used for stabilizing many different pharmaceuticals, of which insulin, vaccines, hyaluronic acid, intralipid, prostaglandin and hormones can be mentioned.

Also a lot of different biological materials can be stabilized according to the invention. However, preferably the biological material is selected from DNA, recombinant DNA, RNA, nucleic acids, biological tissue, transplants, carbohydrates, lipids, membranes, proteins, such as enzymes and plasma proteins, culture media for micro-organisms, cell culture media, blood containing substrates, blood for transfusion, nutrient substrates, insemination media, micro-organisms, seeds, plant parts, spores, fruits and food stuffs.

According to one suitable method for the production of IP$_3$ a material containing IP$_6$ is broken down enzymatically with phytase enzyme. The IP$_6$ can be provided either as pure material or in the form of an IP$_6$ containing source, such as wheat bran. Phytase enzyme can be found for instance in plants, seeds and micro-organisms.

By the enzymatic treatment of the IP$_6$ a hydrolysis takes place resulting in a mixture of different lower inositolphosphates, i.e., inositolpentaphosphate (IP$_5$), inositoltetraphosphate (IP$_4$), inositoltriphosphate (IP$_3$), inositoldiphosphate (IP$_2$) and inositolmonophosphate (IP$_1$).

Usually, the hydrolysis is carried out at a temperature of 20°-70° C. and a pH of 4 to 8. The hydrolysis is suitably stopped when the liberation of about 30-60% of the total ester phosphorus has been achieved. At said stage a high proportion of the desired IP$_3$ isomer or isomers has been formed by hydrolysis of the IP$_6$ containing material.

The mixture of inositolphosphates obtained may hereafter be separated by chromatography to isolate the IP$_3$-containing fraction. Preferably, this is made in a column. If the IP$_3$ fraction contains more than one isomer, these isomers are separated in another subsequent chromatographic separation step.

The IP$_3$ can be obtained as a salt or as an acid thereof. The salt form is preferred, since it is easier to produce in pure and concentrated form than the acid.

The salt form of the IP$_3$ isomer is readily obtainable from the acid form using standard procedures. Thus, there can be prepared salts, such as alkali metal and alkaline earth metal salts, e.g. lithium, sodium, potassium, calcium or magnesium. However, also the aluminium, zinc and iron salts are very useful as well as the NH$_4^+$ and organic amine salts. Exemplary amines are triethanolamine, diethanolamine, triisopropanolamine, N,N-dimethyl-2-amino-2-methyl-1-propanol, N,N-dimethylethanolamine, tetrabutylamine and cyclohexylamine. Also other salts might be used. Especially preferred salts are those which are physiologically acceptable.

The invention is not restricted to any particular isomer of IP$_3$. Consequently, all individual isomers of IP$_3$ and mixtures thereof are included in the above definition, IP$_3$. However, preferably the stabilized composition comprises at least one of D-myo-inositol-1.2.6-triphosphate, D-myo-inositol-1.2.5-triphosphate, myo-inositol-1.2.3-triphosphate, D-myo-inositol-1.4.5-triphosphate and L-myo-inositol-1.3.4-triphosphate. Of these isomers D-myo-inositol-1.2.6-triphosphate is preferred.

When using yeast, preferably baker's yeast as a phytase source, only one isomer of IP$_3$ is obtained; namely D-myo-inositol-1.2.6-triphosphate. Especially when the composition comprises pharmaceuticals it is generally preferred to use the isomer or isomers of IP$_3$ in substantially pure form. The stabilizer component of the composition can consist wholly or essentially of IP$_3$.

The stabilizer is non-toxic and very efficient.

Sometimes the composition can also contain a minor amount of another inositolphosphate, especially inositoldiphosphate, IP$_2$ and inositoltetraphosphate, IP$_4$ in addition to IP$_3$. This is particularly the case where seeds, plant parts, spores, fruits and foodstuff are to be stabilized according to the invention. IP$_2$ and IP$_4$ can be presented in acid as well as in salt form.

The IP$_3$-isomers mentioned above have the following formulas:

D-myo-inositol-1.2.6-triphosphate of the formula

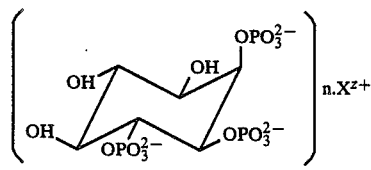

where X is hydrogen, at least one univalent, divalent or multivalent cation, or a mixture thereof, n is the number of ions, and z is the charge of the respectively ion; D-myo-inositol-1.2.5-triphosphate of the formula

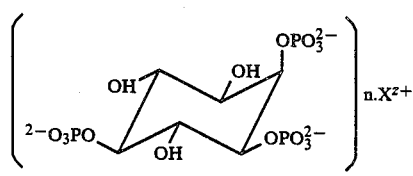

where X, n and z have the above mentioned meaning; myo-inositol-1.2.3-triphosphate of the formula

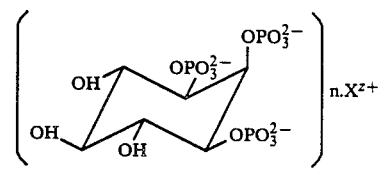

where X, n and z have the above mentioned meaning; L-myo-inositol-1.3.4-triphosphate of the formula

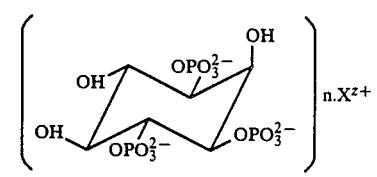

where X, n and z have the above mentioned meaning; and D-myo-inositol-1.4.5-triphosphate of the formula

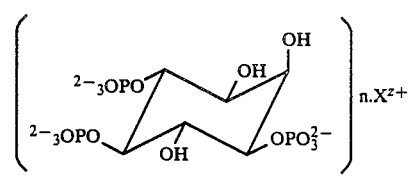

where X, n and z have the above meaning.

In each of the above formulas n ranges between 6 to 1 inclusive and z ranges from 1 to 6 inclusive. Preferably, n is between 3 to 6 inclusive and z is 3, 2 or 1.

For purposes of further understanding the invention, formulas are given below of some of the IP$_3$-isomers of the invention. Formulas are also given for IP$_6$, IP$_5$, IP$_4$ and IP$_2$.

The lower phosphate-esters of myoinositol are named depending on where the phosphoric acid groups are situated on the inositol ring, with the numbering giving as low position numbers as possible. L and D stand for clockwise and counterclock-wise counting respectively, and are used depending on which result gives the lowest position number. The carbon atom which has an axial phosphoric acid group always has the position number 2. The structural formulae below are simplified to the acid form.

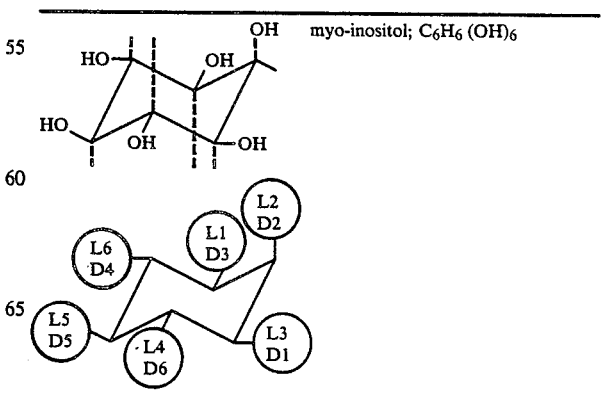

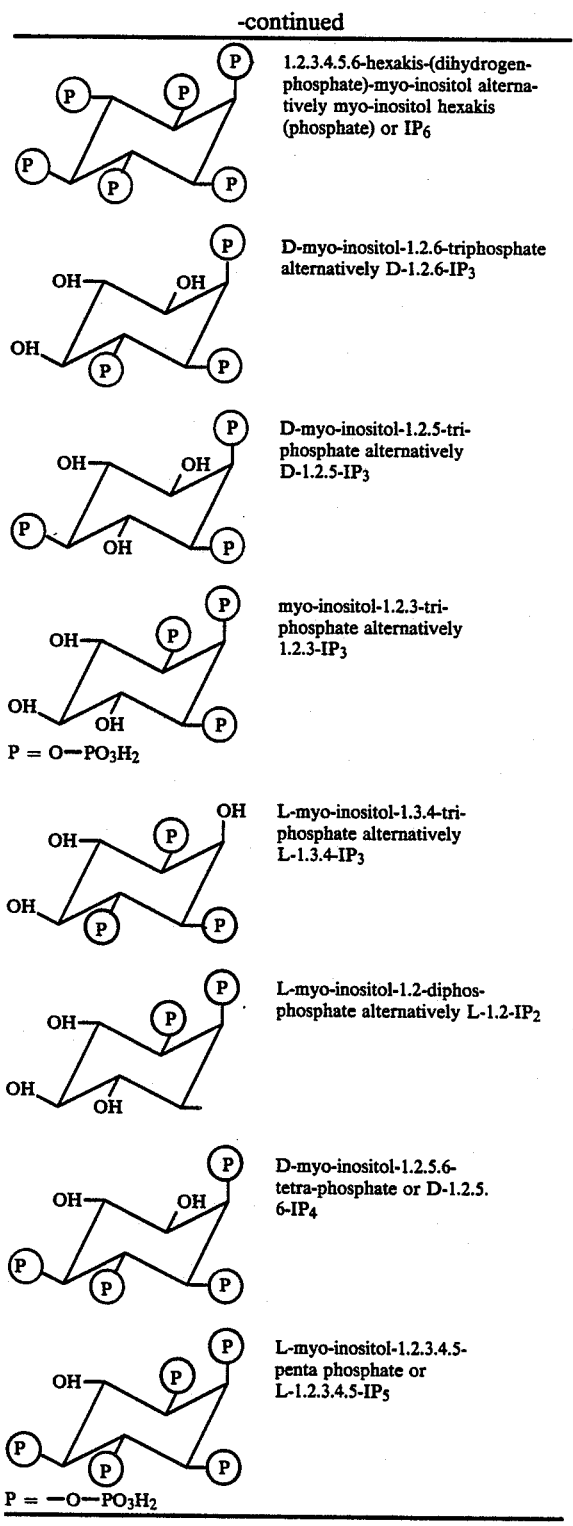

| | |
|---|---|
| | 1.2.3.4.5.6-hexakis-(dihydrogen-phosphate)-myo-inositol alternatively myo-inositol hexakis (phosphate) or IP$_6$ |
| | D-myo-inositol-1.2.6-triphosphate alternatively D-1.2.6-IP$_3$ |
| | D-myo-inositol-1.2.5-triphosphate alternatively D-1.2.5-IP$_3$ |
| | myo-inositol-1.2.3-triphosphate alternatively 1.2.3-IP$_3$ |
| | L-myo-inositol-1.3.4-triphosphate alternatively L-1.3.4-IP$_3$ |
| | L-myo-inositol-1.2-diphosphate alternatively L-1.2-IP$_2$ |
| | D-myo-inositol-1.2.5.6-tetra-phosphate or D-1.2.5.6-IP$_4$ |
| | L-myo-inositol-1.2.3.4.5-penta phosphate or L-1.2.3.4.5-IP$_5$ |

$P = -O-PO_3H_2$

These IP compounds are described and prepared in applicant's copending U.S. patent application, Ser. No. 788,829 filed Oct. 18, 1985.

Other isomers of inositol triphosphate within the contemplation of the present invention include compounds having the structural formula

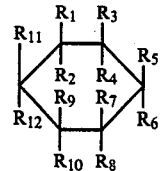

(I)

One group of inositol triphosphate compounds are defined by structural formula (I) where three of $R_1$, $R_3$, $R_5$, $R_7$, $R_{10}$ and $R_{11}$ are hydroxyl and the remaining three are phosphate and $R_2$, $R_4$, $R_6$, $R_8$, $R_9$ and $R_{12}$ are hydrogen.

Another group of inositol triphosphates are defined by structural formula (I) where three of $R_1$, $R_3$, $R_6$, $R_7$, $R_9$ and $R_{12}$ are hydroxyl and the remaining three are phosphate and $R_2$, $R_4$, $R_5$, $R_8$, $R_{10}$ and $R_{11}$ are hydrogen.

Still another group of inositol triphosphates are defined by structural formula (I) where three of $R_1$, $R_3$, $R_5$, $R_8$, $R_{10}$ and $R_{12}$ are hydroxyl and the remaining three are phosphate and $R_2$, $R_4$, $R_6$, $R_7$, $R_9$ and $R_{11}$ are hydrogen.

Yet another group of inositol triphosphates are defined by structural formula (I) where three of $R_1$, $R_4$, $R_5$, $R_8$, $R_9$ and $R_{12}$ are hydroxyl and the remaining three are phosphate and $R_2$, $R_3$, $R_6$, $R_7$, $R_{10}$ and $R_{11}$ are hydrogen.

Still yet another group of inositol triphosphates are defined by structural formula (I) where three of $R_1$, $R_3$, $R_6$, $R_8$, $R_9$ and $R_{12}$ are hydroxyl and the remaining three are phosphate and $R_2$, $R_4$, $R_5$, $R_7$, $R_{10}$ and $R_{11}$ are hydrogen.

Even still another group of inositol triphosphates are defined by structural formula (I) where three of $R_1$, $R_3$, $R_6$, $R_7$, $R_{10}$ and $R_{12}$ are hydroxyl and the remaining three are phosphate and $R_2$, $R_4$, $R_5$, $R_8$, $R_9$ and $R_{11}$ are hydrogen.

Even yet group of inositol triphosphates are defined by structural formula (I) where three of $R_1$, $R_3$, $R_5$, $R_8$, $R_{10}$ and $R_{11}$ are hydroxyl and the remaining three are phosphate and $R_2$, $R_4$, $R_6$, $R_7$, $R_9$ and $R_{12}$ are hydrogen.

Finally, another group of inositol triphosphates are defined by structural formula (I) where three of $R_1$, $R_3$, $R_5$, $R_7$, $R_9$ and $R_{11}$ are hydroxyl and the remaining three are phosphate and $R_2$, $R_4$, $R_6$, $R_8$, $R_{10}$ and $R_{12}$ are hydrogen.

Particular inositol triphosphate compounds within the contemplation of the above groups include compounds having the structural formula (I) where $R_5$, $R_7$ and $R_{10}$ are phosphate, $R_1$, $R_3$ and $R_{11}$ are hydroxyl and $R_2$, $R_4$, $R_6$, $R_8$, $R_9$ and $R_{12}$ are hydrogen;

$R_1$, $R_{10}$ and $R_{11}$ are phosphate, $R_3$, $R_5$ and $R_7$ are hydroxyl and $R_2$, $R_4$, $R_6$, $R_8$, $R_9$ and $R_{12}$ are hydrogen;

$R_1$, $R_3$ and $R_{11}$ are phosphate, $R_5$, $R_7$ and $R_{10}$ are hydroxyl and $R_2$, $R_4$, $R_6$, $R_8$, $R_9$ and $R_{12}$ are hydrogen;

$R_3$, $R_5$ and $R_7$ are phosphate, $R_1$, $R_{10}$ and $R_{11}$ are hydroxyl and $R_2$, $R_4$, $R_6$, $R_8$, $R_9$ and $R_{12}$ are hydrogen;

$R_3$, $R_7$ and $R_{10}$ are phosphate, $R_1$, $R_5$ and $R_{11}$ are hydroxyl and $R_2$, $R_4$, $R_6$, $R_8$, $R_9$ and $R_{12}$ are hydrogen;

$R_3$, $R_{10}$ and $R_{11}$ are phosphate, $R_1$, $R_5$ and $R_7$ are hydroxyl and $R_2$, $R_4$, $R_6$, $R_8$, $R_9$ and $R_{12}$ are hydrogen;

$R_1$, $R_3$ and $R_6$ are phosphate, $R_7$, $R_9$ and $R_{12}$ are hydroxyl and $R_2$, $R_4$, $R_5$, $R_8$, $R_{10}$ and $R_{11}$ are hydrogen;

$R_6$, $R_7$ and $R_9$ are phosphate, $R_1$, $R_3$ and $R_{12}$ are hydroxyl and $R_2$, $R_4$, $R_5$, $R_8$, $R_{10}$ and $R_{11}$ are hydrogen;

$R_3$, $R_5$ and $R_8$ are phosphate, $R_1$, $R_{10}$ and $R_{12}$ are hydroxyl and $R_2$, $R_4$, $R_6$, $R_7$, $R_9$ and $R_{11}$ are hydrogen;

$R_1$, $R_3$ and $R_{12}$ are phosphate, $R_5$, $R_8$ and $R_{10}$ are hydroxyl and $R_2$, $R_4$, $R_6$, $R_7$, $R_9$ and $R_{11}$ are hydrogen;

$R_1$, $R_3$ and $R_5$ are phosphate, $R_8$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_8$ are phosphate, $R_3$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_{12}$ are phosphate, $R_3$, $R_8$ and $R_{10}$ are hydroxyl and $R_2$, $R_4$, $R_6$, $R_7$, $R_9$ an $R_{11}$ are hydrogen;

$R_1$, $R_3$ and $R_{12}$ are phosphate, $R_6$, $R_8$ and $R_9$ are hydroxyl and $R_2$, $R_4$, $R_5$, $R_7$, $R_{10}$ and $R_{11}$ are hydrogen;

$R_1$, $R_3$ and $R_6$ are phosphate, $R_7$, $R_{10}$ and $R_{12}$ are hydroxyl and $R_2$, $R_4$, $R_5$, $R_8$, $R_9$ and $R_{11}$ are hydrogen;

$R_4$, $R_5$ and $R_8$ are phosphate, $R_1$, $R_9$ and $R_{12}$ are hydroxyl and $R_2$, $R_3$, $R_6$, $R_7$, $R_{10}$ and $R_{11}$ are hydrogen;

$R_3$, $R_5$ and $R_8$ are phosphate, $R_1$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_8$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_7$, $R_9$ and $R_{11}$ are hydroxyl and $R_2$, $R_4$, $R_6$, $R_8$, $R_{10}$ and $R_{12}$ are hydrogen;

$R_1$, $R_3$ and $R_{12}$ are phosphate, $R_5$, $R_8$ and $R_9$ are hydroxyl and $R_2$, $R_4$, $R_6$, $R_7$, $R_{10}$ and $R_{11}$ are hydrogen;

$R_1$, $R_3$ and $R_8$ are phosphate, $R_5$, $R_9$, $R_{12}$ are hydroxyl and $R_2$, $R_4$, $R_6$, $R_7$, $R_{10}$ and $R_{11}$ are hydrogen;

$R_3$, $R_5$ and $R_{12}$ are phosphate, $R_1$, $R_8$ and $R_9$ are hydroxyl and $R_2$, $R_4$, $R_6$, $R_7$, $R_{10}$ and $R_{11}$ are hydrogen;

$R_1$, $R_5$ and $R_9$ are phosphate, $R_3$, $R_8$ and $R_{12}$ are hydroxyl and $R_2$, $R_4$, $R_6$, $R_7$, $R_{10}$ and $R_{11}$ are hydrogen;

$R_1$, $R_5$ and $R_{12}$ are phosphate, $R_3$, $R_8$ and $R_9$ are hydroxyl and $R_2$, $R_4$, $R_6$, $R_7$, $R_{10}$ and $R_{11}$ are hydrogen;

$R_1$, $R_3$ and $R_9$ are phosphate, $R_5$, $R_8$ and $R_{12}$ are hydroxyl and $R_2$, $R_4$, $R_6$, $R_7$, $R_{10}$ and $R_{11}$ are hydrogen;

$R_1$, $R_8$ and $R_9$ are phosphate, $R_3$, $R_5$ and $R_{12}$ are hydroxyl and $R_2$, $R_4$, $R_6$, $R_7$, $R_{10}$ and $R_{11}$ are hydrogen;

$R_1$, $R_8$ and $R_{12}$ are phosphate, $R_3$, $R_5$ and $R_9$ are hydroxyl and $R_2$, $R_4$, $R_6$, $R_7$, $R_{10}$ and $R_{11}$ are hydrogen;

$R_5$, $R_8$ and $R_{12}$ are phosphate, $R_1$, $R_3$ and $R_9$ are hydroxyl and $R_2$, $R_4$, $R_6$, $R_7$, $R_{10}$ and $R_{11}$ are hydrogen;

$R_1$, $R_9$ and $R_{12}$ are phosphate, $R_3$, $R_5$ and $R_8$ are hydroxyl and $R_2$, $R_4$, $R_6$, $R_7$, $R_{10}$ and $R_{11}$ are hydrogen;

$R_5$, $R_8$ and $R_9$ are phosphate, $R_1$, $R_3$ and $R_{12}$ are hydroxyl and $R_2$, $R_4$, $R_6$, $R_7$, $R_{10}$ and $R_{11}$ are hydrogen;

$R_3$, $R_8$ and $R_9$ are phosphate, $R_1$, $R_5$ and $R_{12}$ are hydroxyl and $R_2$, $R_4$, $R_6$, $R_7$, $R_{10}$ and $R_{11}$ are hydrogen;

$R_3$, $R_9$ and $R_{12}$ are phosphate, $R_1$, $R_5$ and $R_8$ are hydroxyl and $R_2$, $R_4$, $R_6$, $R_7$, $R_{10}$ and $R_{11}$ are hydrogen;

$R_3$, $R_8$ and $R_{12}$ are phosphate, $R_1$, $R_5$ and $R_9$ are hydroxyl and $R_2$, $R_4$, $R_6$, $R_7$, $R_{10}$ and $R_{11}$ are hydrogen; and $R_8$, $R_9$ and $R_{12}$ are phosphate, $R_1$, $R_3$ and $R_5$ are hydroxyl and $R_2$, $R_4$, $R_6$, $R_7$, $R_{10}$ and $R_{11}$ are hydrogen.

The above discussed compounds having structural formula (I) are made by the same procedure set forth in Examples 19 to 22.

The invention will be explained further in detail in connection with the embodiment examples below, of which examples 1–5 show that $IP_3$ prevents or reduces the formation of free radicals. Example 6 illustrates preservation of some fruits and vegetables at the addition of $IP_3$. Example 7 shows that an addition of $IP_3$ to an enzyme gives a remarkable retention of the enzyme activity at storage. Examples 8–14 show production of $IP_3$ and the separation thereof into different isomers.

EXAMPLE 1

An aqueous solution containing 0.3 mM $FeCl_3$, 5.0 mM ethylenediaminotetraacetic acid (EDTA), 50 mM tris(hydroxymethyl)-aminomethan (TRIS) and 1.0M $NaN_3$ was prepared. In the solution the complex $Fe^{3+}$-EDTA-$N_3$ was formed.

A maximum in absorption of light was detected at the wavelength of 409 nm.

Another aqueous solution containing 0.3 mM $FeCl_3$, 50 mM EDTA and 50 mM TRIS was prepared. In the solution the complex $Fe^{3+}$-EDTA-$H_2O$ was formed. There was no maximum in absorption of light detected at the wavelength of 409 nm.

The above difference in result depends on that $N_3^-$ competitively replaces one water molecular which binds to the $Fe^{3+}$-EDTA-complex. This in turn shows that the $Fe^{3+}$-EDTA-complex has a binding site, which is occupied by a dissociable water-molecule.

It is further known that iron catalyses the formation of hydroxylradicals. For the formation of these the binding of one water molecule to iron is required.

This means that EDTA in the EDTA-$Fe^{3+}$-complex can not inhibit the formation of hydroxyl radicals catalysed by iron.

The above experiment was repeated with the difference that the EDTA was substituted with $IP_3$.

No maximum in absorption was obtained at the wavelength 409 nm.

This result means that the $Fe^{3+}$-complex with $IP_3$ does not bind water. Therefore the formation of free radicals is prevented.

EXAMPLE 2

A reaction mixture consisting of 48 mmol $KH_2PO_4$, 2 mmol Na-ascorbate, 0.1 mmol $H_2O_2$, 0.5 mmol Fe and 1.7 mmol deoxyribose was incubated at 37° C. for 1 hour. Similar reactions mixtures including EDTA 1 mmol or inositol-tri-phosphate ($IP_3$) 1 mmol were similarly incubated. The $IP_3$ used was D-myo-inositol-1.2.6-triphosphate.

After incubation 1.65 ml thiobarbituric acid in 50 mmol NaOH and 1.65 ml 2.8% of trichloroacetic acid was added to 2 ml of the reaction mixture. The mixture was heated to 100° C. for 20 minutes and the absorbance at 532 nm was measured with water as a blank.

The experiments were performed with iron in the form of $Fe^{2+}$ ($Fe(NH_4)SO_4$) and $Fe^{3+}$ ($FeCl_3$). The results were as follows:

Production of free radicals catalyzed by $Fe^{2+}$ and $Fe^{3+}$ in the presence of $IP_3$ or EDTA, expressed as absorbance at 532 nm.

| Group | $Fe^{2+}$ | $Fe^{3+}$ |
|---|---|---|
| Control | 0.76 | 0.79 |
| EDTA | 2.2 | 1.86 |
| $IP_3$ | 0.46 | 0.43 |

These results show that the formation of free radicals in the reaction mixture was diminished by 40% after addition of $IP_3$. The addition of EDTA had an opposite effect. It strongly increased production of free radicals. Thus $IP_3$ was shown to reduce iron-dependent formation of free radicals.

EXAMPLE 3

Lipid peroxidation was studied in lipid micelles. The following reaction mixture was incubated for 2 hours at 37° C.:

| | |
|---|---|
| 0.4 ml | Clark-Lubs buffer pH 5.5 |
| 0.2 ml | phospholipid liposomes |
| 0.1 ml | IP$_3$ 0.5–5 mM or 0.1 ml H$_2$O |
| 0.1 ml | Fe$^{2+}$ 1 mM or 0.1 ml H$_2$O |
| 0.1 ml | Al$^{3+}$ 4 mM or 0.1 ml H$_2$O |
| 0.1 ml | H$_2$O |

The IP$_3$ was D-myo-inositol-1.2.6-triphosphate. After incubation, 0.5 ml of thiobarbituric acid+0.5 ml 25% HCl was added and the mixture was heated at 100° C. for 15 minutes. 1 ml lubrol PX 1% (Sigma) was added and lipid peroxidation was measured by measuring absorbance at 532 nm. The results were as follows:

| | Concentration, mM | | | Absorbance |
|---|---|---|---|---|
| Experiment | Fe$^{2+}$ | Al$^{3+}$ | IP$_3$ | 532 nm |
| 1 | 0.1 | 0 | 0 | 0.36 |
| 2 | 0 | 0.4 | 0 | 0.12 |
| 3 | 0.1 | 0.4 | 0 | 0.89 |
| 4 | 0.1 | 0.4 | 0.5 | 0.36 |
| 5 | 0.1 | 0 | 0.5 | 0.30 |
| 6 | 0.1 | 0 | 0.4 | 0.26 |
| 7 | 0.1 | 0 | 0.2 | 0.29 |
| 8 | 0.1 | 0 | 0.1 | 0.28 |
| 9 | 0.1 | 0 | 0.05 | 0.27 |
| 10 | 0 | 0 | 0 | 0.13 |

Fe$^{2+}$ caused lipid peroxidation (group 1 vs 10). Al$^{3+}$ itself caused no peroxidation (2 vs 10) whereas the combination of Fe$^{2+}$+Al$^{3+}$ caused much stronger peroxidation than Fe$^{2+}$ alone (1 vs 3). Addition of IP$_3$ completely prevented the interaction between Fe$^{2+}$ and Al$^{3+}$ (3 vs 4). In systems with only Fe$^{2+}$, IP$_3$ causes marked reduction in radical formation (1 vs 5–9).

EXAMPLE 4

Lipid peroxidation was studied in lipid micelles. The following reaction mixture was incubated for 2 hours at 37° C.:

| | |
|---|---|
| 0.4 ml | Clark-Lubs buffer pH 5.5 |
| 0.2 ml | phospholipid liposomes |
| 0.1 ml | IP$_3$ 10 mM or 0.1 ml H$_2$O |
| 0.1 ml | Fe$^{2+}$ 1 mM |
| 0.1 ml | Cd$^{2+}$ 1 mM or 1 ml Pb$^{2+}$ 1 mM or 0.1 ml H$_2$O |
| 0.1 ml | H$_2$O |

The IP$_3$ was D-myo-inositol-1.2.6-triphosphate. After incubation, of 0.5 ml of thiobarbituric acid+0.5 ml 25% HCl was added and the mixture was heated at 100° C. for 15 minutes. 1 ml Lubrol PX 1% (Sigma) was added and lipid peroxidation was measured by measuring absorbance at 532 nm. The results were as follows:

| | Concentration, mM | | | Absorbance |
|---|---|---|---|---|
| Experiment | Cd$^{2+}$ | Pb$^{2+}$ | IP$_3$ | 532 nm |
| 1 | 0 | 0 | 0 | 0.63 |
| 2 | 0.1 | 0 | 0 | 1.08 |
| 3 | 0.1 | 0 | 1.0 | 0.73 |
| 4 | 0 | 0.1 | 0 | 1.79 |
| 5 | 0 | 0.1 | 1.0 | 1.32 |

The lipid peroxidation caused by Fe$^{2+}$ (group 1) was strongly increased by Cd (2) and by Pb (4). The effects of both these metals was strongly counteracted by IP$_3$ (3 vs 2 and 5 vs 4).

EXAMPLE 5

Reaction mixtures with the following compositions were incubated for 5 minutes at 37° C.:

| | |
|---|---|
| KH$_2$PO$_4$ buffer pH 7.4 | 20 mM |
| EDTA | 0.1 mM |
| Salicylate | 1 mM |
| Ascorbate | 1 mM |
| H$_2$O$_2$ | 3.3 mM |
| Fe$^{3+}$ | 0.05 mM |
| IP$_3$ | 0, 2.5, 5 or 10 mM |

The products formed by oxidation of salicylate were quantified with HPLC. The IP$_3$ was D-myo-inositol-1.2.6-triphosphate.

The system studies radical scavenging. Under these reaction conditions, all Fe$^{3+}$ will form complex with EDTA. The Fe-EDTA complex will induce free radical formation, and the ability of IP$_3$ to prevent oxidation of salicylate is studied.

The results of the experiment were:

| Concentration of IP$_3$, mM | Relative amount of salicylate oxidized |
|---|---|
| 0 | 100 |
| 2.5 | 44 |
| 5 | 43 |
| 10 | 19 |

Thus, IP$_3$ is able to act as a radical scavenger, thereby preventing free radical induced damage to other molecules.

EXAMPLE 6

Preservation of some fruits and vegetables at the addition of IP$_3$.

4 g of fresh potatoes, bananas and apples respectively were sliced in 10 pieces each. 5 pieces of the same fruit or vegetable were put into each of 5 different beakers. Three of the beakers were filled with 15 ml of an aqueous solution of IP$_3$ and three additional beakers with 15 ml of an aqueous solution of IP$_6$, in such a way that each 5 pieces of fruit and vegetable were exposed either to pure water or water with IP$_3$ and IP$_6$ respectively. The content of IP$_3$ and IP$_6$ respectively in the water was 1.0 g/l.

The samples were allowed to stand in room temperature for 15 hours. After this period the colour of the samples was inspected and the following data were found:

| | Potato | Banana | Apple |
|---|---|---|---|
| No IP$_3$ added | brown colour | brown colour | brown colour |
| IP$_3$ added | very slight brown | very slight brown | slight brown |

| | Potato | Banana | Apple |
|---|---|---|---|
| IP$_6$ added | brown colour | brown colour | brown colour |

The results show that IP$_3$ has a preservative effect on the fruits and vegetables investigated, whereas IP$_6$ has no such effect.

EXAMPLE 7

Enzyme activity at the addition of IP$_3$.

The activity of aldolase with respectively without addition of IP$_3$ was measured as a function of time.

Aldolase degrades fructose-1.6-diphosphate (FDP) as dihydroxyacetonephosphate. This substrate is further reacted by α-glycerophosphatedehydrogenase (GDH) in the presence of nicotinamide adenine dinucleotide, reduced from (NADH) to α-glycerophosphate and nicotinamide adenine dinucleotide, oxidized form (NAD). By measuring the decline of the UV-absorption at 340 nm for the reaction NADH to NAD the activity of the enzyme is determined.

The aldolase was stored at 25° C. and the activity was measured initially and after 72 hours with and without additional of IP$_3$ (4 g/l).

0.5 ul aldolase (A1893 from Sigma Chemical Co, 0.2 U/ml) was mixed with 2.75 ml of a buffer pH 7.5 consisting of 0.10 g KH$_2$PO$_4$, 0.74 K$_2$HPO$_4$, 1.96 KCH$_3$CH$_2$OO, 50 mg FDP and 8 mg NADH per 100 ml buffer. 1.47 ul GDH was further added and the total volume was diluted to 3.0 ml. The determination of the activity was performed at 30° C.

The following results were obtained:

| Time for storage at 25° C. | No Ip$_3$ added | IP$_3$ added |
|---|---|---|
| 0 | 0.12 | 0.12 decline of absorbance/min |
| 72 hours | 0.05 | 0.07 decline of absorbance/min |

The results show that the activity of the enzyme was improved by about 40% after addition of IP$_3$ when the activity was determined after 72 hours storage at 25° C.

EXAMPLE 8

Hydolysis of sodium phytate with wheat phytase and fractionation of a mixture of inositolphosphates.

A 1.6 gram quantity of sodium phytate (from corn, Sigma Chemical Co) was dissolved in 650 ml sodium acetate buffer, pH 5.2. 2.7 gram wheat phytase (EC 3.1.3.26, 0.015 U/mg, from Sigma Chemical Co) was added and the mixture was incubated at 38° C.

The dephosphorylation was followed by determining the inorganic phosphorus released. After 3 hours when 50% inorganic phosphorus was liberated the hydrolysis was stopped by adding 30 ml ammonia to pH 12. A liquid mixture containing inositolphosphates was obtained.

350 ml of the mixture was passed through an ion-exchange column (Dowex 1, chloride form, 25 mm×250 mm) and eluted with a linear gradient of hydrochloric acid (0–0.7N HCl). Aliquots of eluted fractions were completely hydrolyzed in order to determine the contents of phosphorus and inositol. The peaks correspond to different inositolphosphates i.e. a peak with the ratio of phosphorus to inositol of three to one consists of inositoltriphosphate etc. Two fractions with the ratio of phosphorus to inositol of three to one were obtained.

EXAMPLE 9

Fractionation of inositoltriphosphates.

100 ml of the first fraction obtained in Example 8 with a phosphorus/inositol ratio of three to one was neutralized and precipitated as a bariumsalt after addition of 10% excess of 0.1M bariumacetate solution. 600 mg of the precipitated salt was dissolved in 50 ml 0.18N hydrochloric acid. The solution was separated on an ion-exchange column (Dowex 1, chloride form, 25 mm×2500 mm) with diluted hydrochloric acid as eluent. Aliquots of eluted fractions were analyzed for phosphorus. Three peaks consisting of isomers of inositoltriphosphates can be seen. EXAMPLE 10

Structural determination of isomers of inositol-triphosphates with NMR.

The three peaks obtained in Example 9 were analyzed by H-NMR. Data show that the peaks consist of myo-inositol-1.2.6-triphosphate, myo-inositol-1.2.3-triphosphate and myo-inositol-1.3.4-triphosphate respectively.

The second fraction obtained in Example 18 with a phosphorus/inositol ratio of three to one was analyzed by H-NMR. Data show that the fraction consists of myo-inositol-1.2.5-triphosphate.

EXAMPLE 11

Determination of optical isomers of inositol-triphosphates.

20 mg of the compounds determined with NMR according to Example 10 to be myo-inositol-1.2.6-triphosphate and myo-inositol-1.3.4-triphosphate were further chromatographed on a chiral column based on acetylated cellulose (20 mm×300 mm from Merck) with a mixture of ethanol and water as eluent. The fractions were analyzed with a polarimeter. As can be seen each compound consists of one optical isomer, D-myo-inositol-1.2.6-triphosphate and L-myo-inositol-1.3.4-triphosphate respectively.

EXAMPLE 12

Hydrolysis of sodium phytate with baker's yeast and fractionation of a mixture of inositolphosphates.

A 0.7 gram quantity of sodium phytate (from corn, Sigma Chemical Co) was dissolved in 600 ml sodium acetate buffer pH 4.6. 50 gram of baker's yeast from Jästbolaget, Sweden (dry substance: 28%, nitrogen content: 2%; phosphorus content: 0.4%) was added with stirring and incubation was continued at 45° C. The dephosphorylation was followed by determining the inorganic phosphorus released. After 7 hours when 50% inorganic phosphorus was liberated the hydrolysis was stopped by adding 30 ml of ammonia to pH 12. The suspension was centrifuged and the supernatant was collected.

400 ml of the supernatant was passed through an ion-exchange column (Dowex 1, chloride form, 25 mm×250 mm) and eluted with a linear gradient of hydrochloric acid (0–0.7N HCl).

Aliquots of eluted fractions were completely hydrolyzed in order to determine the contents of phosphorus and inositol. The peaks correspond to different inositolphosphates i.e. a peak with the ratio of phosphorus to inositol of three to one consists of inositoltriphosphates etc.

EXAMPLE 13

Structural determination of isomers of inositoltriphosphate.

The fraction obtained in Example 12 with a phosphorus/inositol ratio of three to one was neutralized and evaporated before analysis with H-NMR. Data show that the peak consists of myo-inositol-1.2.6-triphosphate.

EXAMPLE 14

Determination of optical isomers of myo-inositol-triphosphate.

The same method was used as described in Example 11 with the difference that 10 mg of the compound determined with NMR according to Example 13 was analyzed. As can be seen the compound consists of one optical isomer, D-myo-inositol-1.2.6-triphosphate.

EXAMPLE 15

A reaction mixture containing, in a final volume of 2 ml, the following reagents: 50 mM $KH_2PO_4$ buffer (pH=7.4), 0.5 mM Ascorbate, 0.05 mM $Fe^{3+}$, 0.2 mM or 0.5 mM $H_2O_2$ and 1.7 mM Deoxyribose was incubated at 37° C. for 1 hour. Similar reaction mixtures including 0.5 mM or 1.0 mM D-myo-inositol-1.2.6-triphosphate were similarly incubated.

After incubation 1.65 ml 1% (w/v) thiobarbituric acid in 50 mM NaOH and 1.65 ml 2.8% (w/v) trichloroacetic acid were added. The mixture was healed to 100° C. for 20 minutes and the absorbance at 532 nm was measured against water as a blank.

Production of free radicals catalyzed by $Fe^{3+}$ in presence of different concentrations of $IP_3$ expressed as absorbance at 532 nm gave the following results:

| Group | Absorbance |
| --- | --- |
| 0.2 mM $H_2O_2$ Control | 0.322 |
| 0.2 mM $H_2O_2$ + 0.5 mM $IP_3$ | 0.153 |
| 0.2 mM $H_2O_2$ + 1.0 mM $IP_3$ | 0.130 |
| 0.5 mM $H_2O_2$ Control | 0.553 |
| 0.5 mM $H_2O_2$ + 0.5 mM $IP_3$ | 0.332 |
| 0.5 mM $H_2O_2$ + 1.0 mM $IP_3$ | 0.324 |

These results show that at 0.2 mM $H_2O_2$ addition of 0.5 mM $IP_3$ diminish the production of free radicals by 50% and 1.0 mM $IP_3$ diminish it by 60%. At 0.5 mM $H_2O_2$ both 0.5 mM and 1.0 mM $IP_3$ decreased the radical production by 40%.

EXAMPLE 16

A reaction mixture containing, in a final volume of 2 ml, the following reagents: 50 mM $KH_2PO_4$ buffer (pH=7.4), 0.05 mM $Fe^{3+}$, 2.0 mM Deoxyribose, 0.3 mM Hypoxantine and 42 mU/ml Xantineoxidase was incubated at 37° C. for 1 hour. The blanks were incubated in the absence of enzyme. Similar reaction mixtures including 0.2 mM, 0.5 mM or 1.0 mM D-myo-inositol-1.2.6-triphosphate were similarly incubated.

After incubation 1.65 ml 1% (w/v) thiobarbituric acid in 50 mM NaOH and 1.65 ml 2.8% (w/v) trichloroacetic acid was added. To the blanks was also Xantineoxidase added. The mixtures were heated at 100° C. for 20 minutes and the absorbance at 532 nm was measured.

Production of free radicals formed by Xantineoxidase and catalyzed by $Fe^{3+}$ in the presence of $IP_3$ gave the following results:

| Group | Absorbance (difference between reaction mixture and blank) |
| --- | --- |
| Control | 0.339 |
| 0.2 mM $IP_3$ | 0.232 |
| 0.5 mM $IP_3$ | 0.153 |
| 1.0 mM $IP_3$ | 0.108 |

The results show that $IP_3$ inhibits also the enzyme catalyzed free radical formation. The efficiency of the inhibition depends on the concentration of $IP_3$.

EXAMPLE 17

A reaction mixture containing, in a final volume of 1 ml, the following reagents: 50 mM TRIS buffer (pH=7.4), 0.05 mM $Fe^{3+}$, 50 mM DMSO (dimethylsulfoxide), 0.3 mM Hypoxantine and 18 mU Xantineoxidase was incubated at 37° C. for 30 minutes. The blanks were incubated in the absence of enzyme. Similar reaction mixture including 0.5 mM D-myo-inositol-1.2.6-triphosphate was similarly incubated.

Reaction was terminated by the addition of 50 ul 100% trichloroacetic acid. Xantineoxidase was then added to the blanks. Formation of formaldehyde was measured by addition of 1.05 ml Hantzsch solution (Hantzsch solution consists of 50 mM acetic acid, 20 mM acetylacetone and 2M ammoniumacetate). The mixtures were then incubated 40 minutes at 37° C. and the absorbance was measured at 412 nm.

Production of free radicals formed by Xantineoxidase and catalyzed by $Fe^{3+}$ in the presence of $IP_3$ gave the following results.

| Group | Absorbance (difference between reaction mixture and blank) |
| --- | --- |
| Control | 0.072 |
| 0.5 mM $IP_3$ | 0.008 |

These results show a nearly complete 90% inhibition of the free radical formation.

EXAMPLE 18

A reaction mixture containing, in a final volume of 2 ml, the following reagents: 50 mM TRIS buffer (pH=7.4), 0.5 mM Ascorbate, 0.05 mM $Fe^{3+}$, 0.5 mM $H_2O_2$ and 5 mM DMSO was incubated at 37° C. for 1 hour. Similar reaction mixtures including 0.5 mM or 1.0 mM D-myo-inositol-1.2.6-triphosphate were similarly incubated.

After incubation 0.1 ml 90% Trichloroacetic acid and 2.1 ml Hantzsch solution was added. (Hantzsch solution consists of 50 mM acetic acid, 20 mM acetylacetone and 2M ammoniumacetate). The samples were then incubated 40 minutes at 37° C. and the absorbance was measured at 412 nM against water as a blank.

Production of free radicals catalyzed by $Fe^{3+}$ in presence of different concentrations of $IP_3$ expressed as absorbance at 412 nm gave the following results:

| Group | Absorbance |
| --- | --- |
| Control | 0.445 |

| Group | Absorbance |
| --- | --- |
| 0.5 mM IP$_3$ | 0.351 |
| 1.0 mM IP$_3$ | 0.323 |

Also in this system the results show that the formation of free radicals was inhibited by IP$_3$, at 0.5 mM IP$_3$ to 20% and at 1.0 mM IP$_3$ to 30%.

EXAMPLE 19

A 0.5 gram quantity of D-chiro-inositol was dissolved in 1 mL phosphoric acid at 60° C. 20 g polyphosphoric acid was added and the mixture was heated to 150° C. under vacuum for 6 hours. The mixture was diluted with water to a volume of 200 ml and passed through an ion-exchange column (Dowex 1, chloride form, 25 mm×250 mm) and eluted with a linear gradient of hydrochloric acid (0–2.0N HCl).

The content of the peak with the ratio of phosphorus to inositol of six to one was precipitated by addition of calciumhydroxide. The precipitate was filtered, washed and mixed with 10 ml of a cation-exchange resin to give the acid form of the inositolhexaphosphate. After neutralization with sodium hydroxide and freeze-drying the sodiumsalt of D-chiro-inositolhexaphosphate was obtained.

EXAMPLE 20

A 0.8 gram quantity of the sodium salt of D-chiro-inositolhexaphosphate produced according to Example 19 was dissolved in 300 ml sodium acetate buffer, pH 5.2. 1.3 gram wheat phytase (EC 3.1.3.26 0.015 U/mg from Sigma Chemical Co.) was added and the mixture was incubated at 38° C.

After the liberation of 50% inorganic phosphorus the hydrolysis was stopped by adding ammonia to pH 12.

The mixture containing D-chiro-inositolphosphates was passed through an ion-exchange column (Dowex 1 chloride form, 25 mm×250 mm) and eluted with a linear gradient of hydrochloric acid (0–0.7N HCl).

The peak with the ratio of phosphorus to inositol of three to one was neutralized with 1.0M sodium hydroxide and freeze-dried.

Structural determination with NMR and IR showed the product to be D-chiro-inositoltriphosphate.

EXAMPLE 21

A 0.8 gram quantity of epi-inositol was dissolved in 1.5 ml of phosphoric acid at 60° C. 32 g polyphosphoric acid was added and the mixture was heated to 150° C. under vacuum for 6 hours. The mixture was diluted with water to a volume of 200 ml and passed through an ion-exchange column (Dowex 1, chloride form, 25 mm×250 mm) and eluted with a linear gradient of hydrochloric acid (0–2.0N HCl).

The content of the peak with the ratio of phosphorus to inositol of six to one was precipitated by addition of calcium hydroxide. The precipitate was filtered, washed and mixed with 10 ml of a cation-exchange resin to give the acid form of the inositol hexaphosphate. After neutralization with sodium hydroxide and freeze-drying the sodium salt of epi-inositolhexaphosphate was obtained.

EXAMPLE 22

A 1.2 gram quantity of the sodium salt of epi-inositolhexaphosphate produced according to Example 21 was dissolved in 500 ml sodium acetate buffer, pH 5.2. 2.0 gram wheat phytase (EC 3.1.3.26, 0.015 U/mg from Sigma Chemical Co.) was incubated at 38° C.

After the liberation of 50% inorganic phosphorus the hydrolysis was stopped by adding ammonia to pH 12.

The mixture containing epi-inositolphosphates was passed through an ion-exchange column (Dowex 1, chloride form, 25 mm×250 mm) and eluted with a linear gradient of hydrochloric acid (0–0.7N HCl).

The peak with the ratio of phosphorus to inositol of three to one was neutralized with 1.0M sodium hydroxide and freeze-dried.

Structural determination with NMR and IR showed the product to be epi-inositoltriphosphate.

What is claimed is:

1. A stabilized composition comprising an organic substrate subject to degradation by oxidation and/or free radical reaction and between about 0.01% to about 2% by weight, based on the total weight of the composition, of at least one isomer of inositol triphosphate, a salt thereof or an acid thereof, said isomer having the structural formula

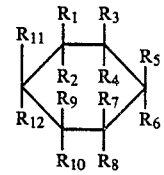

where
(a) three of $R_1$, $R_3$, $R_5$, $R_7$, $R_{10}$ and $R_{11}$ are hydroxyl and the remaining three are phosphate and $R_2$, $R_4$, $R_6$, $R_8$, $R_9$ and $R_{12}$ are hydrogen;
(b) three of $R_1$, $R_3$, $R_6$, $R_7$, $R_9$ and $R_{12}$ are hydroxyl and the remaining three are phosphate and $R_2$, $R_4$, $R_5$, $R_8$, $R_{10}$ and $R_{11}$ are hydrogen;
(c) three of $R_1$, $R_3$, $R_5$, $R_8$, $R_{10}$ and $R_{12}$ are hydroxyl and the remaining three are phosphate and $R_2$, $R_4$, $R_6$, $R_7$, $R_9$ and $R_{11}$ are hydrogen;
(d) three of $R_1$, $R_4$, $R_5$, $R_8$, $R_9$ and $R_{12}$ are hydroxyl and the remaining three are phosphate and $R_2$, $R_3$, $R_6$, $R_7$, $R_{10}$ and $R_{11}$ are hydrogen;
(e) three of $R_1$, $R_3$, $R_6$, $R_8$, $R_9$ and $R_{12}$ are hydroxyl and the remaining three are phosphate and $R_2$, $R_4$, $R_5$, $R_7$, $R_{10}$ and $R_{11}$ are hydrogen;
(f) three of $R_1$, $R_3$, $R_6$, $R_7$, $R_{10}$ and $R_{12}$ are hydroxyl and the remaining three are phosphate and $R_2$, $R_4$, $R_5$, $R_8$, $R_9$ and $R_{11}$ are hydrogen;
(g) three of $R_1$, $R_3$, $R_5$, $R_8$, $R_{10}$ and $R_{11}$ are hydroxyl and the remaining three are phosphate and $R_2$, $R_4$, $R_6$, $R_7$, $R_9$ and $R_{12}$ are hydrogen; or
(h) three of $R_1$, $R_3$, $R_7$, $R_9$ and $R_{11}$ are hydroxyl and the remaining three are phosphate and $R_2$, $R_4$, $R_6$, $R_8$, $R_{10}$ and $R_{12}$ are hydrogen.

2. A composition according to claim 1 wherein $R_5$, $R_7$ and $R_{10}$ are phosphate, $R_1$, $R_3$ and $R_{11}$ are hydroxyl and $R_2$, $R_4$, $R_6$, $R_8$, $R_9$ and $R_{12}$ are hydrogen.

3. A composition according to claim 1 wherein $R_1$, $R_{10}$ and $R_{11}$ are phosphate, $R_3$, $R_5$ and $R_7$ are hydroxyl and $R_2$, $R_4$, $R_6$, $R_8$, $R_9$ and $R_{12}$ are hydrogen.

4. A composition according to claim 1 wherein $R_1$, $R_3$ and $R_{11}$ are phosphate, $R_5$, $R_7$ and $R_{10}$ are hydroxyl and $R_2$, $R_4$, $R_6$, $R_8$, $R_9$ and $R_{12}$ are hydrogen.

5. A composition according to claim 1 wherein $R_3$, $R_5$ and $R_7$ are phosphate, $R_1$, $R_{10}$ and $R_{11}$ are hydroxyl and $R_2$, $R_4$, $R_6$, $R_8$, $R_9$ and $R_{12}$ are hydrogen.

6. A composition according to claim 1 wherein $R_3$, $R_7$ and $R_{10}$ are phosphate, $R_1$, $R_5$ and $R_{11}$ are hydroxyl and $R_2$, $R_4$, $R_6$, $R_8$, $R_9$ and $R_{12}$ are hydrogen.

7. A composition according to claim 1 wherein $R_3$, $R_{10}$ and $R_{11}$ are phosphate, $R_1$, $R_5$ and $R_7$ are hydroxyl and $R_2$, $R_4$, $R_6$, $R_8$, $R_9$ and $R_{12}$ are hydrogen.

8. A composition according to claim 1 wherein $R_1$, $R_3$ and $R_6$ are phosphate, $R_7$, $R_9$ and $R_{12}$ are hydroxyl and $R_2$, $R_4$, $R_5$, $R_8$, $R_{10}$ and $R_{11}$ are hydrogen.

9. A composition according to claim 1 wherein $R_6$, $R_7$ and $R_9$ are phosphate, $R_1$, $R_3$ and $R_{12}$ are hydroxyl and $R_2$, $R_4$, $R_5$, $R_8$, $R_{10}$ and $R_{11}$ are hydrogen.

10. A composition according to claim 1 wherein $R_3$, $R_5$ and $R_8$ are phosphate, $R_1$, $R_{10}$ and $R_{12}$ are hydroxyl and $R_2$, $R_4$, $R_6$, $R_7$, $R_9$ and $R_{11}$ are hydrogen.

11. A composition according to claim 1 wherein $R_1$, $R_3$ and $R_{12}$ are phosphate, $R_5$, $R_8$ and $R_{10}$ are hydroxyl and $R_2$, $R_4$, $R_6$, $R_7$, $R_9$ and $R_{11}$ are hydrogen.

12. A composition according to claim 1 wherein $R_1$, $R_3$ and $R_5$ are phosphate, $R_8$, $R_{10}$ and $R_{12}$ are hydroxyl and $R_2$, $R_4$, $R_6$, $R_7$, $R_9$ and $R_{11}$ are hydrogen.

13. A composition according to claim 1 wherein $R_1$, $R_5$ and $R_8$ are phosphate, $R_3$, $R_{10}$ and $R_{12}$ are hydroxyl and $R_2$, $R_4$, $R_6$, $R_7$, $R_9$ and $R_{11}$ are hydrogen.

14. A composition according to claim 1 wherein $R_1$, $R_5$ and $R_{12}$ are phosphate, $R_3$, $R_8$ and $R_{10}$ are hydroxyl and $R_2$, $R_4$, $R_6$, $R_7$, $R_9$ and $R_{11}$ are hydrogen.

15. A composition according to claim 1 wherein $R_1$, $R_3$ and $R_{12}$ are phosphate, $R_6$, $R_8$ and $R_9$ are hydroxyl and $R_2$, $R_4$, $R_5$, $R_7$, $R_{10}$ and $R_{11}$ are hydrogen.

16. A composition according to claim 1 wherein $R_1$, $R_3$ and $R_6$ are phosphate, $R_7$, $R_{10}$ and $R_{12}$ are hydroxyl and $R_2$, $R_4$, $R_5$, $R_8$, $R_9$ and $R_{11}$ are hydrogen.

17. A composition according to claim 1 wherein $R_4$, $R_5$ and $R_8$ are phosphate, $R_1$, $R_9$ and $R_{12}$ are hydroxyl and $R_2$, $R_3$, $R_6$, $R_7$, $R_{10}$ and $R_{11}$ are hydrogen.

18. A composition according to claim 1 wherein $R_3$, $R_5$ and $R_8$ are phosphate, $R_1$, $R_{10}$ and $R_{11}$ are hydroxyl and $R_2$, $R_4$, $R_6$, $R_7$, $R_9$ and $R_{12}$ are hydrogen.

19. A composition according to claim 1 wherein $R_1$, $R_3$ and $R_5$ are phosphate, $R_8$, $R_{10}$ and $R_{11}$ are hydroxyl and $R_2$, $R_4$, $R_6$, $R_7$, $R_9$ and $R_{12}$ are hydrogen.

20. A composition according to claim 1 wherein $R_1$, $R_3$ and $R_5$ are phosphate, $R_7$, $R_9$ and $R_{11}$ are hydroxyl and $R_2$, $R_4$, $R_6$, $R_8$, $R_{10}$ and $R_{12}$ are hydrogen.

21. A stabilized composition comprising an organic substrate subject to degradation by oxidation and/or free radical reaction and between about 0.01% to about 2% by weight, based on the total weight of the composition, of inositol triphosphate, said inositol triphosphate provided by at least one compound, a salt thereof or an acid having the structural formula

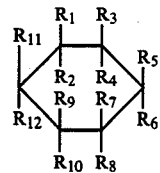

where
(a) $R_1$, $R_3$ and $R_{12}$ are phosphate; $R_5$, $R_8$ and $R_9$ are hydroxyl; and $R_2$, $R_4$, $R_6$, $R_7$, $R_{10}$ and $R_{11}$ are hydrogen;

(b) $R_1$, $R_3$ and $R_8$ are phosphate; $R_5$, $R_9$ and $R_{12}$ are hydroxyl; and $R_2$, $R_4$, $R_6$, $R_7$ and $R_{10}$ and $R_{11}$ are hydrogen;

(c) $R_3$, $R_5$ and $R_{12}$ are phosphate; $R_1$, $R_8$, and $R_9$ are hydroxyl; and $R_2$, $R_4$, $R_6$, $R_7$, $R_{10}$ and $R_{11}$ are hydrogen;

(d) $R_1$, $R_5$ and $R_9$ are phosphate; $R_3$, $R_8$ and $R_{12}$ are hydroxyl; and $R_2$, $R_4$, $R_6$, $R_7$, $R_{10}$ and $R_{11}$ are hydrogen;

(e) $R_1$, $R_3$ and $R_9$ are phosphate; $R_5$, $R_8$ and $R_{12}$ are hydroxyl; and $R_2$, $R_4$, $R_6$, $R_7$, $R_{10}$ and $R_{11}$ are hydrogen;

(f) $R_1$, $R_8$ and $R_9$ are phosphate; $R_3$, $R_5$, and $R_{12}$ are hydroxyl; and $R_2$, $R_4$, $R_6$, $R_7$, $R_{10}$ and $R_{11}$ are hydrogen;

(g) $R_1$, $R_8$ and $R_{12}$ are phosphates; $R_3$, $R_5$ and $R_9$ are hydroxyl; and $R_2$, $R_4$, $R_6$, $R_7$, $R_{10}$ and $R_{11}$ are hydrogen;

(h) $R_5$, $R_8$ and $R_{12}$ are phosphate; $R_1$, $R_3$ and $R_9$ are hydroxyl; and $R_2$, $R_4$, $R_6$, $R_7$, $R_{10}$ and $R_{11}$ are hydrogen;

(i) $R_1$, $R_9$ and $R_{12}$ are phosphate; $R_3$, $R_5$ and $R_8$ are hydroxyl; and $R_2$, $R_4$, $R_6$, $R_7$, $R_{10}$ and $R_{11}$ are hydrogen;

(j) $R_5$, $R_8$ and $R_9$ are phosphate; $R_1$, $R_3$ and $R_{12}$ are hydroxyl; $R_2$, $R_4$, $R_6$, $R_7$, $R_{10}$ and $R_{11}$ are hydrogen;

(k) $R_3$, $R_8$ and $R_9$ are phosphate; $R_1$, $R_5$ and $R_{12}$ are hydroxyl; and $R_2$, $R_4$, $R_6$, $R_7$, $R_{10}$ and $R_{11}$ are hydrogen;

(l) $R_3$, $R_8$ and $R_{12}$ are phosphate; $R_1$, $R_5$ and $R_9$ are hydroxyl; and $R_2$, $R_4$, $R_6$, $R_7$, $R_{10}$, and $R_{11}$ are hydrogen;

(m) $R_8$, $R_9$ and $R_{12}$ are phosphate; $R_1$, $R_3$ and $R_5$ are hydroxyl; and $R_2$, $R_4$, $R_6$, $R_7$, $R_{10}$ and $R_{11}$ are hydrogen (n) $R_1$, $R_5$ and $R_{12}$ are phosphate; $R_3$, $R_8$ and $R_9$ are hydroxyl; and $R_2$, $R_4$, $R_6$, $R_7$, $R_{10}$ and $R_{11}$ are hydrogen; or (o) $R_3$, $R_9$ and $R_{12}$ are phosphate; $R_1$ and $R_5$ and $R_8$ are hydroxyl; and $R_2$, $R_4$, and $R_6$, $R_7$, $R_{10}$ and $R_{11}$ are hydrogen.

* * * * *

UNITED STATES PATENT AND TRADEMARK OFFICE
CERTIFICATE OF CORRECTION

PATENT NO. : 4,793,945

DATED : December 27, 1988

INVENTOR(S) : Matti Siren

It is certified that error appears in the above-identified patent and that said Letters Patent is hereby corrected as shown below:

Column 3, line 37: "another inositolphosphate" should read as -- other inositolphosphates --.

Column 5, line 60: "IP" should read as $--IP_3--$

Column 8, line 17: "molecular" should read as --molecule--

Column 9, line 40: "causes" should read as --caused--

Column 9, line 56: "incubation, of 0.5" should read as --incubation, 0.5--

Column 11, line 18: "from" should read as --form--

Column 11, line 26: "additional" should read as --addition--

Column 11, line 37: "$I_{p3}$" should read as $--IP_3--$

UNITED STATES PATENT AND TRADEMARK OFFICE
CERTIFICATE OF CORRECTION

PATENT NO. : 4,793,945

DATED : December 27, 1988

INVENTOR(S) : Matti Siren

It is certified that error appears in the above-identified patent and that said Letters Patent is hereby corrected as shown below:

Column 12, line 16: move "EXAMPLE 10" to line 18

Column 16, line 54: "$R_3$, $R_7$," should read as --$R_3$, $R_5$, $R_7$,--

Signed and Sealed this

Twenty-sixth Day of June, 1990

*Attest:*

*Attesting Officer*

HARRY F. MANBECK, JR.

Commissioner of Patents and Trademarks